US012642572B2

(12) United States Patent
Zhao et al.

(10) Patent No.: US 12,642,572 B2
(45) Date of Patent: Jun. 2, 2026

(54) COMPUTER VISION BASED CONTROL OF AN ENERGY GENERATOR

(71) Applicant: Covidien LP, Mansfield, MA (US)

(72) Inventors: Jing Zhao, Superior, CO (US); Daniel A. Joseph, Golden, CO (US); Christopher T. Brown, Boulder, CO (US)

(73) Assignee: Covidien LP, Mansfield, MA (US)

( * ) Notice: Subject to any disclaimer, the term of this patent is extended or adjusted under 35 U.S.C. 154(b) by 327 days.

(21) Appl. No.: 18/277,417

(22) PCT Filed: Feb. 9, 2022

(86) PCT No.: PCT/US2022/015772
§ 371 (c)(1),
(2) Date: Aug. 16, 2023

(87) PCT Pub. No.: WO2022/186959
PCT Pub. Date: Sep. 9, 2022

(65) Prior Publication Data
US 2024/0122638 A1 Apr. 18, 2024

Related U.S. Application Data

(60) Provisional application No. 63/155,801, filed on Mar. 3, 2021.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1445* (2013.01); *G06T 7/0012* (2013.01);
(Continued)

(58) Field of Classification Search
CPC . A61B 18/08; A61B 18/1206; A61B 18/1442; A61B 18/1445; A61B 2018/126; A61B 2018/00589; A61B 34/30
See application file for complete search history.

(56) References Cited

U.S. PATENT DOCUMENTS

2009/0261804 A1* 10/2009 McKenna .......... A61B 18/1447
                                                        324/71.1
2012/0136347 A1* 5/2012 Brustad .............. A61B 18/1445
                                                        606/46
(Continued)

FOREIGN PATENT DOCUMENTS

EP         3669796 A1     6/2020

OTHER PUBLICATIONS

Carter, James E: "Suture? Staple? Electrosurgery? How to Decide What is Best For You", Journal of the Society of Saparoendoscopic Surgeons, vol. 1, No. 2, Apr. 1, 1997 (Apr. 1, 1997), pp. 171-174, XP055922121, US ISSN: 1086-8089.
(Continued)

*Primary Examiner* — Daniel W Fowler

(57) ABSTRACT

An electrosurgical instrument includes a pair of jaws, an endoscope configured to capture image data of a surgical site including the electrosurgical instrument, and an energy generator coupled to the electrosurgical instrument. The energy generator is configured to generate an energy output to the electrosurgical instrument. The system also includes an endoscope controller which includes a processor and a memory. The memory includes instructions stored thereon, which, when executed by the processor, cause the energy-based surgical system to access the captured image, determine a thickness of tissue grasped by the pair of jaws based on the image, and control the energy output of the energy generator based on the determined thickness.

19 Claims, 8 Drawing Sheets

600

(51) Int. Cl.

| | |
|---|---|
| *G06T 7/00* | (2017.01) |
| *G06T 7/60* | (2017.01) |
| *A61B 1/00* | (2006.01) |
| *A61B 18/00* | (2006.01) |
| *A61B 90/00* | (2016.01) |

(52) U.S. Cl.

CPC .......... *G06T 7/60* (2013.01); *A61B 1/000096* (2022.02); *A61B 2018/00642* (2013.01); *A61B 2018/00702* (2013.01); *A61B 2018/00982* (2013.01); *A61B 2090/061* (2016.02); *A61B 2090/067* (2016.02); *A61B 2090/3937* (2016.02); *G06T 2207/10068* (2013.01); *G06T 2207/30204* (2013.01)

(56) References Cited

U.S. PATENT DOCUMENTS

| | | | | |
|---|---|---|---|---|
| 2016/0270842 | A1* | 9/2016 | Strobl | ................ A61B 18/1445 |
| 2017/0065351 | A1 | 3/2017 | Case et al. | |
| 2019/0099262 | A1* | 4/2019 | Ladas | .................. A61B 3/0025 |
| 2019/0298398 | A1* | 10/2019 | Wellman | ............. A61B 17/282 |
| 2020/0237237 | A1 | 7/2020 | Mozdzierz | |
| 2020/0237452 | A1* | 7/2020 | Wolf | ...................... G06F 3/048 |
| 2021/0196368 | A1* | 7/2021 | Pope | ................. A61B 18/1233 |

OTHER PUBLICATIONS

International Search Report and Written Opinion dated May 30, 2022, issued in corresponding PCT International Appln. No. PCT/US2022/015772, 16 pages.

* cited by examiner

700 ⟍

800 ⟍

COMPUTER VISION BASED CONTROL OF AN ENERGY GENERATOR

BACKGROUND

Technical Field

The present disclosure relates to an energy-based surgical system having an energy generator that is controlled using machine vision, and in particular, extracting visual cue data from a video stream and controlling the energy generator based on the visual cue data.

Background of Related Art

Electrosurgery involves application of high radio frequency (RF) electrical current to a surgical site to cut, ablate, desiccate, or coagulate tissue. In monopolar electrosurgery, a source or active electrode delivers radio frequency alternating current from the energy generator to the targeted tissue. A patient return electrode is placed remotely from the active electrode to conduct the current back to the generator.

In bipolar electrosurgery, return, and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes. Electrosurgical instruments are also used in laparoscopic surgery, where the clinician has limited view due to the presence of a single viewpoint supplied by an endoscope. Ultrasonic instruments are also used, which include ultrasonic transducers that vibrate waveguides and attached end effectors, e.g., sealers and/or dissectors, to seal or dissect tissue due to heat imparted by rapid movement of the end effectors. Ultrasound is controlled by closure of jaw and extent of vibration and multiple energy or lengths of tip displacement are used to seal or cut tissue between the jaws or cut tissue in contact with the end of the jaws. Other thermal devices less commonly used include lasers in direct contact or stand off from the tissue target designed to coagulate or ablate using either high or low energy pulses. Additionally, ferromagnetic, or positive thermal coefficient heating of a tissue contacting element have been used to cut, coagulate, seal or thermally necrose.

Energy delivery may be controlled using algorithms, which utilize voltage and/or current-based closed loop control schemes. Algorithms only control energy delivery and do not prevent activation of the instruments beyond the field of view (e.g., in laparoscopic surgery) or activation of the instrument in various misuse conditions such as clamping on large tissue bundles, or other situations which may result in inadvertent injury of tissues.

Thus, there is a need for novel automated control algorithms that utilize advancements in computer vision technology utilizing machine learning to add context to the electrosurgical control schemes.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the disclosure, energy-based surgical system is disclosed, which includes an electrosurgical instrument having a pair of jaws, an endoscope configured to capture image data of a surgical site including the electrosurgical instrument, and an energy generator coupled to the electrosurgical instrument. The energy generator is configured to generate an energy output to the electrosurgical instrument. The system also includes an endoscope controller which includes a processor and a memory. The memory includes instructions stored thereon, which, when executed by the processor, cause the energy-based surgical system to access the captured image, determine a thickness of tissue grasped by the pair of jaws based on the image, and control the energy output of the energy generator based on the determined thickness.

In an aspect of the present disclosure, the electrosurgical instrument may include at least two markers, wherein one marker of the at least two markers is disposed on one of the jaws. When determining the thickness of the tissue, the instructions, when executed, may further cause the energy-based surgical system to recognize the at least two markers and estimate the angle of the jaws based on the recognized markers.

In another aspect of the present disclosure, the at least two markers may infrared readable markers and/or visible light readable markers.

In yet another aspect of the present disclosure, when determining the thickness of the tissue, the instructions when executed may further cause the energy-based surgical system to determine tissue conductivity based on the estimated angle.

In a further aspect of the present disclosure, when determining the thickness of the tissue, the instructions, when executed, may further cause the energy-based surgical system to control the energy output of the energy generator based on the determined tissue conductivity.

In yet a further aspect of the present disclosure, when determining the thickness of the tissue, the instructions, when executed, may further cause the energy-based surgical system to determine tissue type based on estimated tissue conductivity.

In accordance with aspects of the disclosure, wherein when determining the thickness of the tissue, the instructions, when executed, may further cause the energy-based surgical system to determine tissue type based on estimated tissue conductivity.

In an aspect of the present disclosure, when determining the thickness of the tissue, the instructions, when executed, may further cause the energy-based surgical system to control the energy output of the energy generator based on the determined tissue type.

In another aspect of the present disclosure, the instructions, when executed, may further cause the energy-based surgical system to determine if the estimated angle is greater than a predetermined value and initiate an electrosurgical mode prior to initiating a seal cycle, based on the determination. The energy generator may further be configured to select the electrosurgical mode based on a configuration of the electrosurgical instrument.

In yet another aspect of the present disclosure, the instructions, when executed, may further cause the energy-based surgical system to adjust seal cycle parameters based on the estimated jaw angle.

In a further aspect of the present disclosure, the determining may be performed by a machine learning network.

In accordance with aspects of the disclosure, a computer-implemented method for controlling an energy generator includes capturing image data of a surgical site and an electrosurgical instrument through an endoscope, the electrosurgical instrument including a pair of jaws, determining a thickness of tissue grasped by the pair of jaws based on the image, outputting radio frequency (RF) energy to the electrosurgical instrument from an energy generator, and controlling RF energy based on the determined thickness.

In yet a further aspect of the present disclosure, the electrosurgical instrument includes at least two markers, with one of the at least two markers being disposed on one of the jaw. When determining the thickness of the tissue the method may further include recognizing the at least two markers and estimating the angle of the jaws based on the recognized markers.

In accordance with aspects of the disclosure, the at least two markers may include infrared readable markers or visible light readable markers.

In an aspect of the present disclosure, when determining the thickness of the tissue, the method may further include determining tissue conductivity based on the estimated angle.

In another aspect of the present disclosure, when determining the thickness of the tissue, the method may further include controlling the energy output of the energy generator based on the determined tissue conductivity.

In yet another aspect of the present disclosure, when determining the thickness of the tissue, the method may further include determining tissue type based on estimated tissue conductivity.

In a further aspect of the present disclosure, when determining the thickness of the tissue, the method may further include controlling the energy output of the energy generator based on the determined tissue type.

In yet a further aspect of the present disclosure, the method may further include determining if the estimated angle is greater than a predetermined value and initiating an electrosurgical mode prior to initiating a seal cycle, based on the determination, wherein the energy generator is further configured to select the electrosurgical mode based on a configuration of the electrosurgical instrument.

In an aspect of the present disclosure, the method may further include adjusting seal cycle parameters based on the estimated jaw angle.

In accordance with aspects of the disclosure, a non-transitory computer-readable storage medium in which is stored instructions for causing a processor to execute a computer-implemented method for controlling an energy generator, the method including capturing image data of a surgical site and an electrosurgical instrument through an endoscope, wherein the electrosurgical instrument includes a pair of jaws, determining a thickness of tissue grasped by the pair of jaws based on the image, outputting radio frequency (RF) energy to the electrosurgical instrument from an energy generator, and controlling RF energy based on the determined thickness.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
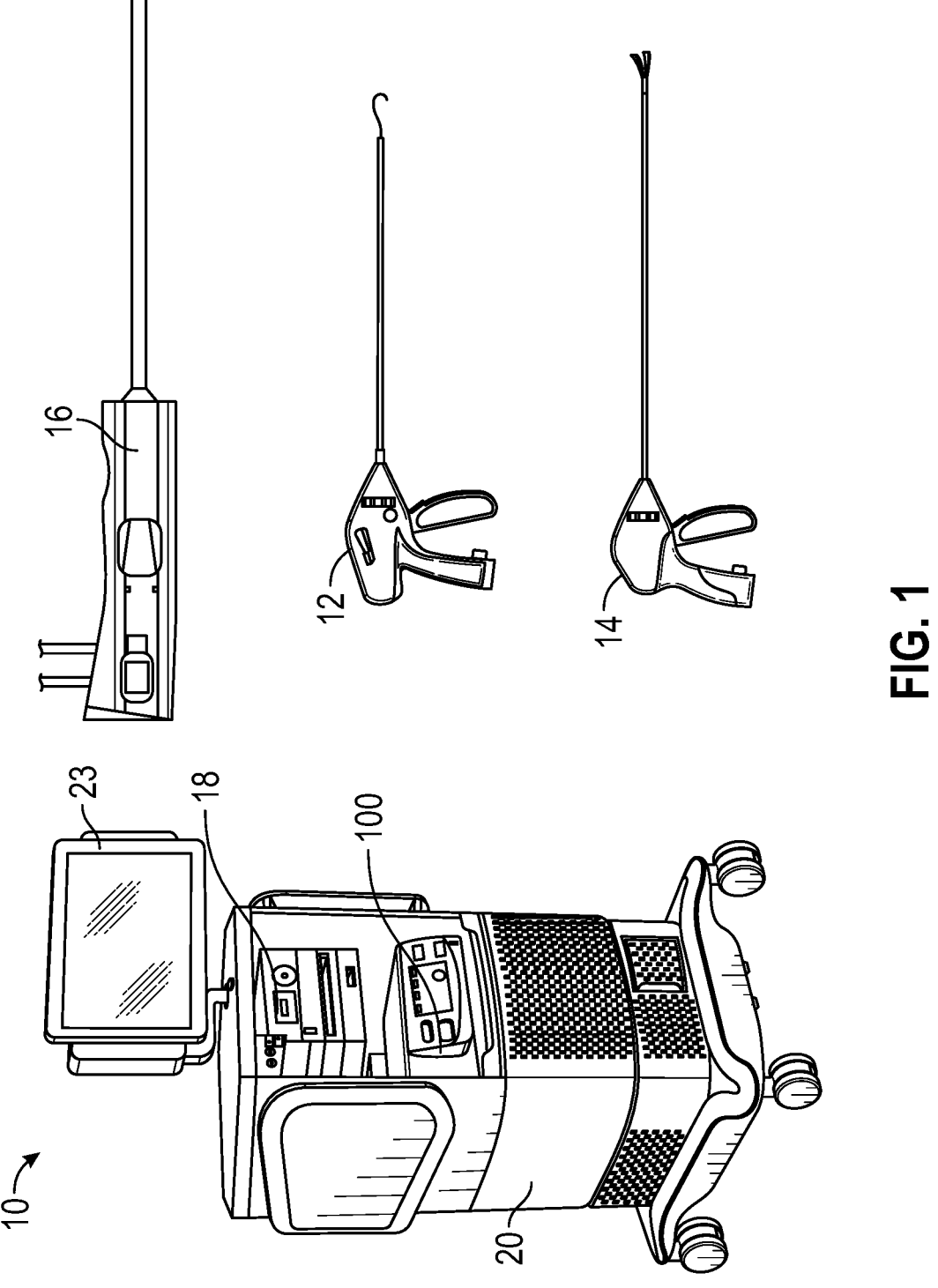
FIG. 1 is a perspective view of an energy-based surgical system, according to an aspect of the present disclosure.

Aspects of the presently disclosed energy-based surgical system are described in detail with reference to the drawings, in which like reference numerals designate identical or corresponding elements in each of the several views. As used herein, the term "distal" refers to the portion of the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software that would be understood by one skilled in the art to be an application. An application may run on a controller or on a user device, including, for example, a mobile device, an IoT device, a server system, or any programmable logic device.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An energy generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Referring to FIG. 1, an energy-based surgical system 10 is shown, which may include a plurality of electrosurgical instruments, such as a first electrosurgical instrument 12, a second electrosurgical instrument 14, and an endoscope 16. The first and second electrosurgical instruments 12 and 14 may be monopolar, bipolar, or hybrid (monopolar and bipolar), such as LIGASURE™ instruments available from Medtronic, Minneapolis, MN. Instrument 12 may be a hybrid instrument and may include a pair of jaws each having an electrode and used as bipolar forceps and an extendible monopolar electrode. Instrument 14 may be a bipolar forceps instrument having a pair of jaws each having an electrode. In aspects of the present disclosure, the instrument 14 may be an ultrasonic instrument, e.g., vessel sealer/dissector. The endoscope 16 may be an endoscopic camera that is coupled to an endoscope controller 18, which also provides light through a fiberoptic cable. The first and second electrosurgical instruments 12 and 14 are coupled to an energy generator 100. The endoscope controller 18 and the energy generator 100 are disposed in a control tower 20, which includes a display 23, which may be a touchscreen, and outputs the video feed from the endoscope 16 as well as various the graphical user interfaces (GUIs).

Figure 2:
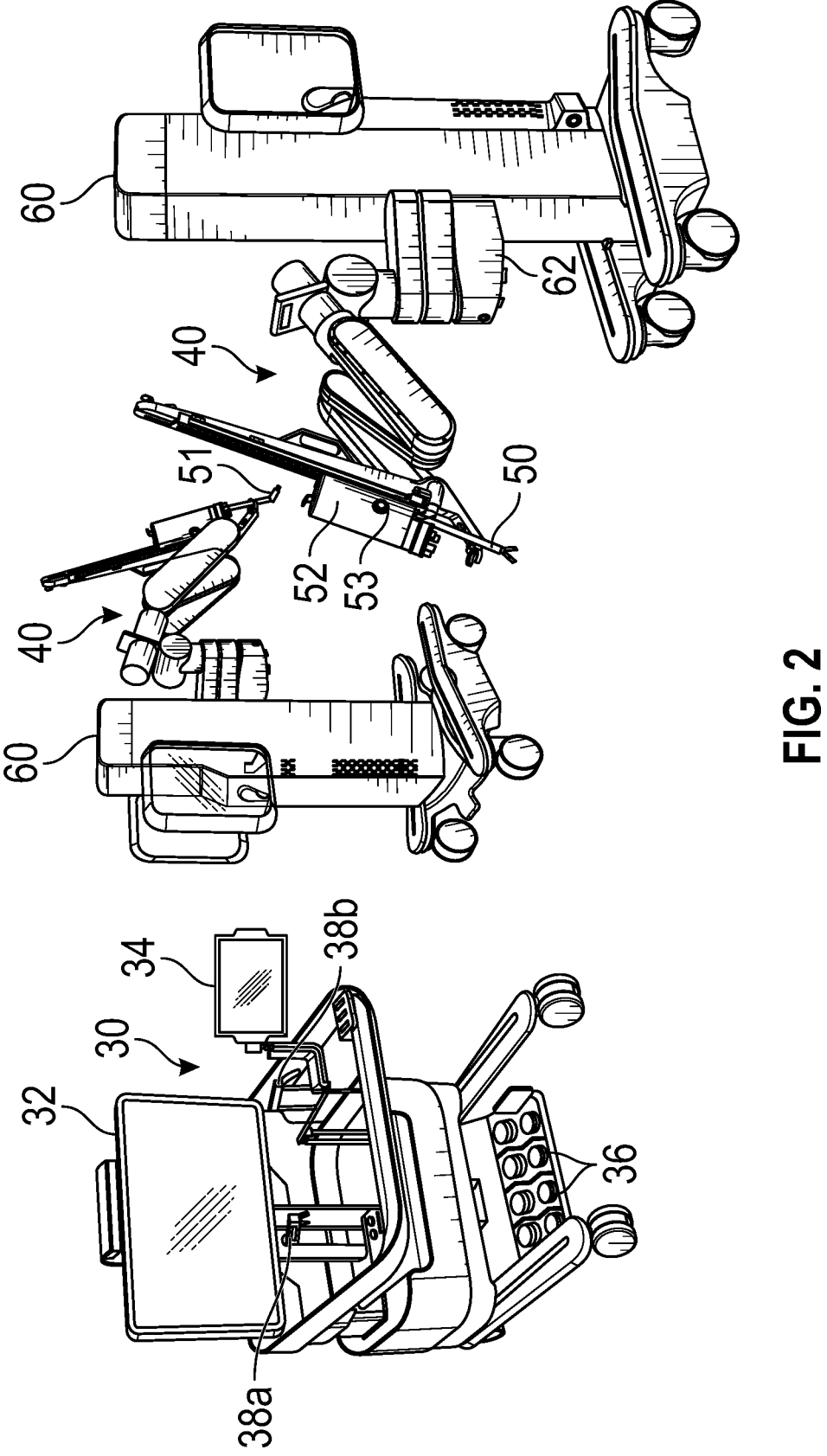
FIG. 2 is a perspective view of a surgical robotic system for use with the energy-based surgical system, according to an aspect of the present disclosure.

With reference to FIG. 2, the energy-based surgical system 10 may also be used as part of a surgical robotic system 10. The control tower 20 is connected to all of the components of the surgical robotic system 10, including a surgical console 30 and one or more robotic arms 40. Each of the robotic arms 40 includes a surgical instrument 50 (e.g., first and second electrosurgical instruments 12 and 14) removably coupled thereto. Each of the robotic arms 40 is also coupled to a movable cart 60.

The endoscope 16 is coupled to one of the robotic arms 40. The endoscope 16 is configured to capture video of the surgical site. The surgical console 30 includes a first display 32, which displays a video feed of the surgical site provided by camera 51 of the surgical instrument 50 disposed on the robotic arms 40, and a second interaction display 34, which displays a user interface for controlling the surgical robotic system 10. The first and second displays 32 and 34 are touchscreens allowing for displaying various graphical user inputs.

The surgical console 30 also includes a plurality of user interface devices, such as pedals 36 and a pair of handle controllers 38a and 38b which are used by a user to remotely control robotic arms 40. The surgical console further includes an armrest used to support clinician's arms while operating the handle controllers 38a and 38b.

The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer (not shown), which are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/ internet protocol (UDP/IP), and/or datagram congestion control protocol (DCCP). Wireless communication may be achieved via one or more wireless configurations, e.g., radio frequency—embedded millimeter-wave transverse optical, Wi-Fi, Bluetooth (an open wireless protocol for exchanging data over short distances, using short length radio waves, from fixed and mobile devices, creating personal area networks (PANs), ZigBee® (a specification for a suite of high-level communication protocols using small, low-power digital radios based on the IEEE 122.15.4-2003 standard for wireless personal area networks (WPANs)).

The computers of the robotic system 10 and the endoscope controller 18 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 3:
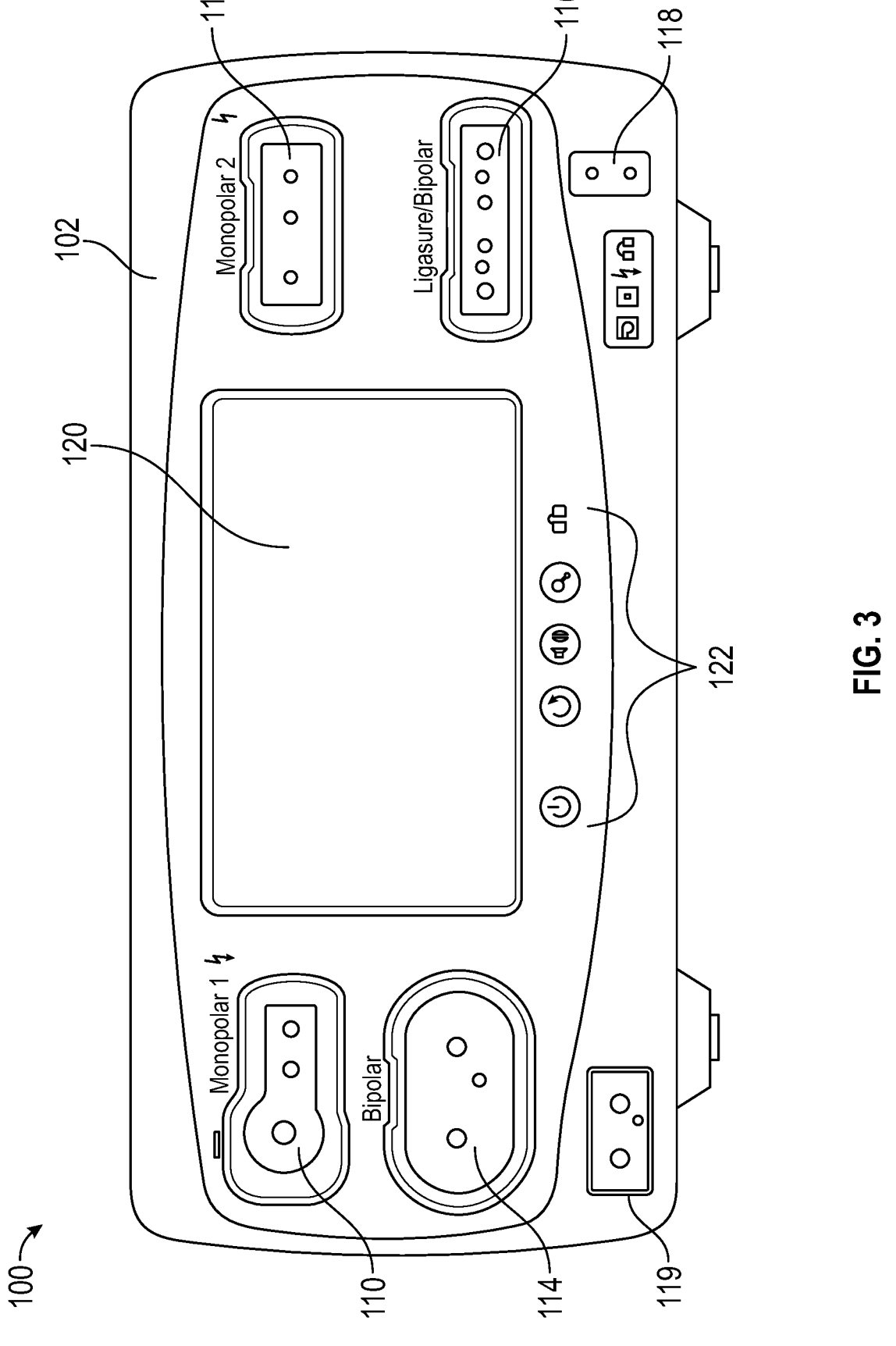
FIG. 3 is a front view of an energy generator of FIG. 1, according to an aspect of the present disclosure.

With reference to FIG. 3, a front face 102 of the generator 100 is shown. The generator 100 may include a plurality of ports 110, 112, 114, 116 to accommodate various types of electrosurgical instruments and a port 118 for coupling to a return electrode pad and a port 119 configured to couple to a footswitch. The ports 110 and 112 are configured to couple to the monopolar electrosurgical instruments (e.g., first electrosurgical instrument 12). The ports 114 and 116 are configured to couple to bipolar electrosurgical instruments (e.g., second electrosurgical instrument 14). The generator 100 includes a display 120 for providing the user with variety of output information (e.g., intensity settings, treatment complete indicators, etc.). The display 120 is a touchscreen configured to display a menu corresponding to each of the ports 110, 112, 114, 116 and the instrument coupled. The user also adjusts inputs by touching corresponding menu options. The generator 100 also includes suitable input controls 122 (e.g., buttons, activators, switches, touch screen, etc.) for controlling the generator 100.

The generator 100 is configured to operate in a variety of modes and is configured to output monopolar and/or bipolar waveforms corresponding to the selected mode. Each of the modes may be activated by the buttons disposed on the first and second electrosurgical instrument 12 and 14. Each of the modes operates based on a preprogrammed power curve that limits how much power is output by the generator 100 at varying impedance ranges of the load (e.g., tissue). Each of the power curves includes power, voltage and current control ranges that are defined by the user-selected intensity setting and the measured minimum impedance of the load.

The generator 100 may operate in the following monopolar modes, which include, but are not limited to, cut, blend, division with hemostasis, fulgurate and spray. The generator 100 may operate in the following bipolar modes, including bipolar cutting, bipolar coagulation, automatic bipolar which operates in response to sensing tissue contact, and various algorithm-controlled vessel sealing modes. The generator 100 may be configured to deliver energy required to power an ultrasonic transducer. Thereby enabling control and modulation of ultrasonic surgical instruments.

Each of the RF waveforms may be either monopolar or bipolar RF waveforms, each of which may be continuous or discontinuous and may have a carrier frequency from about 200 kHz to about 500 kHz. As used herein, continuous waveforms are waveforms that have a 100% duty cycle. In aspects of the present disclosure, continuous waveforms are used to impart a cutting effect on tissue. Conversely, discontinuous waveforms are waveforms that have a non-continuous duty cycle, e.g., below 100%. In aspects of the present disclosure, discontinuous waveforms are used to provide coagulation effects to tissue.

Figure 4:
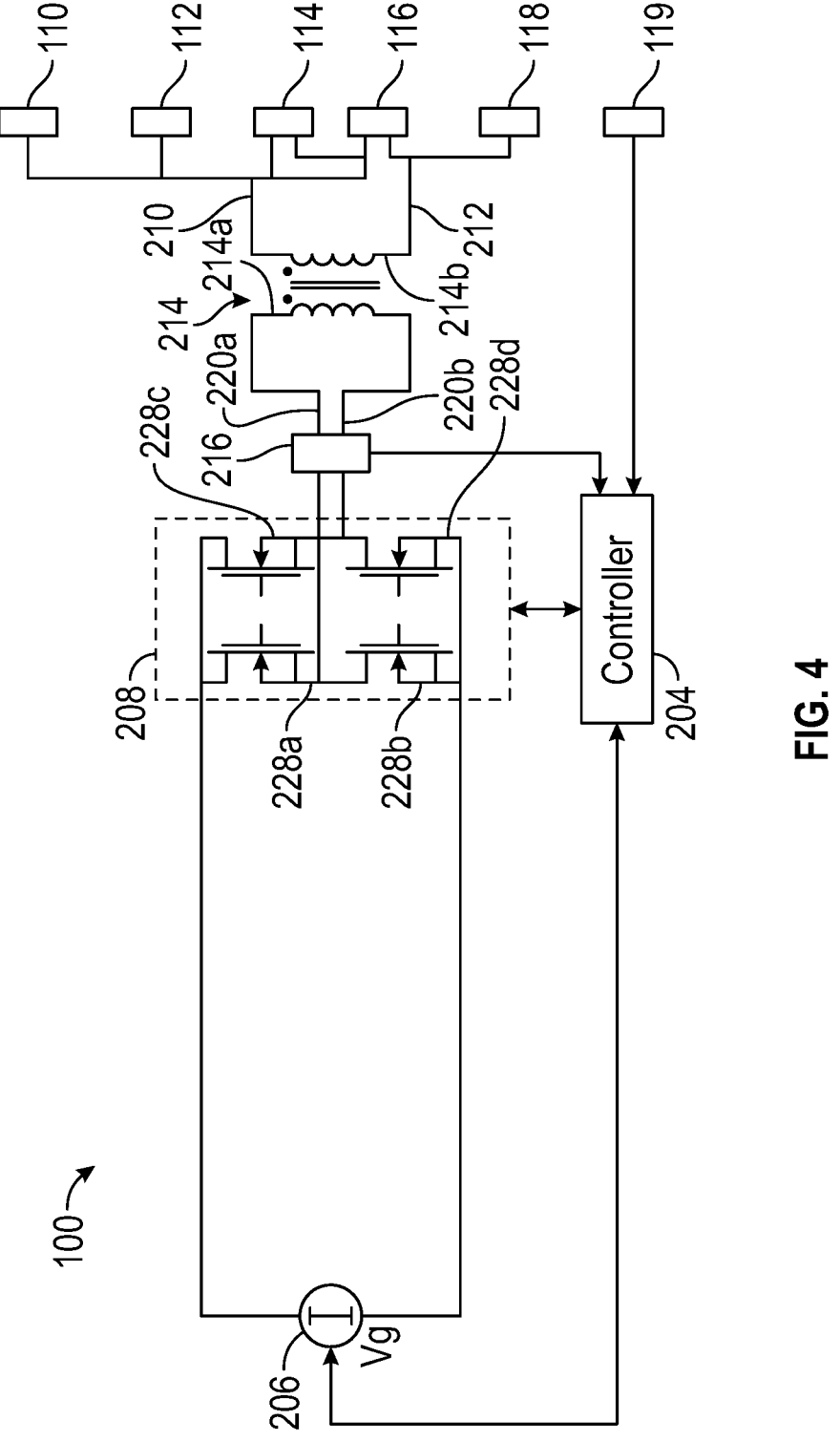
FIG. 4 is a schematic diagram of the energy generator of FIG. 1, according to an aspect of the present disclosure.

With reference to FIG. 4, the generator 100 includes a controller 204, a power supply 206, and a RF inverter 208. The power supply 206 may be high voltage, DC power supplies connected to a common AC source (e.g., line voltage) and provide high voltage, DC power to their respective RF inverter 208, which then convert DC power into a RF waveform through active terminal 210 and return terminal 212 corresponding to the selected mode.

The active terminal 210 and the return terminal 212 are coupled to the RF inverter 208 through an isolation transformer 214. The isolation transformer 214 includes a primary winding 214a coupled to the RF inverter 208 and a secondary winding 214b coupled to the active and return terminals 210 and 212.

Electrosurgical energy for energizing the monopolar electrosurgical instrument 12 is delivered through the ports 110 and 112, each of which is coupled to the active terminal 210. RF energy is returned through the return electrode pad coupled to the port 118, which in turn, is coupled to the return terminal 212. The secondary winding 214b of the isolation transformer 214 is coupled to the active and return terminals 210 and 212. RF energy for energizing a bipolar electrosurgical instrument is delivered through the ports 114 and 116, each of which is coupled to the active terminal 210 and the return terminal 212. The generator 100 may include a plurality of steering relays or other switching devices configured to couple the active terminal 210 and the return terminals 212 to various ports 110, 112, 114, 116, 118 based on the combination of the monopolar and bipolar electrosurgical instruments 12 and 14 being used.

The RF inverter 208 is configured to operate in a plurality of modes, during which the generator 100 outputs corresponding waveforms having specific duty cycles, peak voltages, crest factors, etc. It is envisioned that in other aspects, the generator 100 may be based on other types of suitable power supply topologies. RF inverter 208 may be a resonant RF amplifier or non-resonant RF amplifier, as shown. A non-resonant RF amplifier, as used herein, denotes an amplifier lacking any tuning components, i.e., conductors, capacitors, etc., disposed between the RF inverter and the load, e.g., tissue.

The controller 204 may include a processor (not shown) operably connected to a memory (not shown) similar to the processors used in computers of the robotic system 10. The controller 204 is operably connected to the power supply 206 and/or RF inverter 208 allowing the processor to control the output of the RF inverter 208 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to the controller 204. The controller 204 then controls the power supply 206 and/or RF inverter 208, which adjust the DC and/or RF waveform, respectively.

The generator 100 according to the present disclosure may also include a plurality of sensors 216, each of which monitors output of the RF inverter 208 of the generator 100. The sensor 216 may be any suitable voltage, current, power, and impedance sensors. The sensors 216 are coupled to leads 220a and 220b of the RF inverter 208. The leads 220a and 220b couple the RF inverter 208 to the primary winding 214a of the transformer 214. Thus, the sensors 216 are configured to sense voltage, current, and other electrical properties of energy supplied to the active terminal 210 and the return terminal 212.

In further aspects, the sensor 216 may be coupled to the power supply 206 and may be configured to sense properties of DC current supplied to the RF inverter 208. The controller 204 also receives input (e.g., activation) signals from the display 120, the input controls 122 of the generator 100 and/or the instruments 12 and 14. The controller 204 adjust power outputted by the generator 100 and/or perform other control functions thereon in response to the input signals.

The RF inverter 208 includes a plurality of switching elements 228a-228d, which are arranged in an H-bridge topology. In aspects of the present disclosure, RF inverter 208 may be configured according to any suitable topology, including, but not limited to, half-bridge, full-bridge, push-pull, and the like. Suitable switching elements include voltage-controlled devices such as transistors, field-effect transistors (FETs), combinations thereof, and the like. In aspects of the present disclosure, the FETs may be formed from gallium nitride, aluminum nitride, boron nitride, silicon carbide, or any other suitable wide bandgap materials.

The controller 204 is in communication with the RF inverter 208, and in particular, with the switching elements 228a-228d. Controller 204 is configured to output control signals, which may be pulse-width modulated ("PWM") signals, to switching elements 228a-228d. In particular, controller 204 is configured to modulate a control signal supplied to switching elements 228a-228d of the RF inverter 208. The control signal provides PWM signals that operate the RF inverter 208 at a selected carrier frequency. Additionally, controller 204 are configured to calculate power characteristics of output of the RF inverter 208 of the generator 100 and control the output of the generator 100 based at least in part on the measured power characteristics including, but not limited to, voltage, current, and power at the output of RF inverter 208.

The present disclosure provides for receiving and analyzing the video stream from the endoscope 16 at the endoscope controller 18 to extract visual cue data (e.g., an opening angle of a pair of jaws) from the video stream and make decisions based on the visual cue data, for example, adjusting energy output from the generator 100 (FIG. 1). The endoscope 16 may have a stereoscopic camera. In aspects of the present disclosure, the endoscope 16 may include an infrared (IR) source and a camera capable of capturing IR light and using the data to enhance the video feed. In further aspects, thermal imaging, ultraviolet light image, and/or multi-spectral imaging devices may also be embedded in the endoscope 16. Furthermore, fiducials, markers, tracers, and contrast agents may be used to enhance imaging and object detection. The endoscope controller 18 may also incorporate additional imaging techniques such as depth mapping, laser speckle imaging for flow mapping, etc. This visual cue data may include, for example, but is not limited to, detection of fiducial markers on the jaw of an instrument in the field of view (FOV) of the endoscope.

Visual cue data may be obtained using a computer vision algorithm derived from machine learning techniques, such as a deep neural network trained to recognize identity, position, orientation, operational state of instruments 12 and 14 in the field of view of the endoscope 16 and other contextual parameters described above. The deep learning neural network for classifying images (i.e., extract visual cue data) may include a convolutional neural network (CNN) and/or a recurrent neural network. Generally, a deep learning neural network includes multiple hidden layers. The deep learning neural network may leverage one or more CNNs to classify one or more images, taken by the endoscope 16. In various methods, the one or more CNNs may have a different amount of classification from each other. For example, a first CNN may have a five-class CNN, and a second CNN may have a six-class CNN. The deep learning neural network may be executed on the endoscope controller 18.

The endoscope controller 18 is also coupled to the generator 100 and provides the visual cue data to the generator 100. In aspects of the present disclosure, the controller 204 of the generator is configured to execute a control algorithm configured to perform one or more of the following automatic actions, including but not limited to, raising a visual warning on the display 23 and or display 120, raising a haptic warning through the instruments 12 and 14, enabling or disabling an energy mode to prevent inadvertent activation out of FOV (beyond view, behind something, etc.), enabling or disabling an energy mode to prevent inadvertent activation near sensitive tissue structures, enabling or disabling an energy mode to prevent inadvertent activation near other instruments or implanted devices, switching energy modes, e.g., from monopolar to bipolar, RF to ultrasonic, isolated seal mode to bulk seal mode, modulating energy intensity, triggering sensors within the generator 100, the instruments 12 and 14, or another device, and triggering collection of data from the generator 100 or the endoscope 16.

During operation, there may be multiple triggering events. The endoscope controller 18 is configured to determine to change, disable or modify the RF energy output based on a first trigger event and disable or modify event is further modified or reversed based on a second trigger event following the first trigger event.

The control algorithm may be overridden by the clinician, including but not limited to, pressing a button or sequence of buttons, contextual based override where the output from the algorithm may be overridden by another algorithm, safety-based override to maintain proper function of instruments. In response to an override, the control algorithm may then take one or more of the following actions, including but not limited to, raising an audio and/or visual warning on the video feed source shown on the display 23 of the control tower 20 and/or GUI shown on the display 120 of the generator 100. Similarly, the controller 204 may provide haptic feedback to the instrument 12 or 14. In addition, an override may trigger collection of data relevant to the surrounding time period and event.

Figure 5:
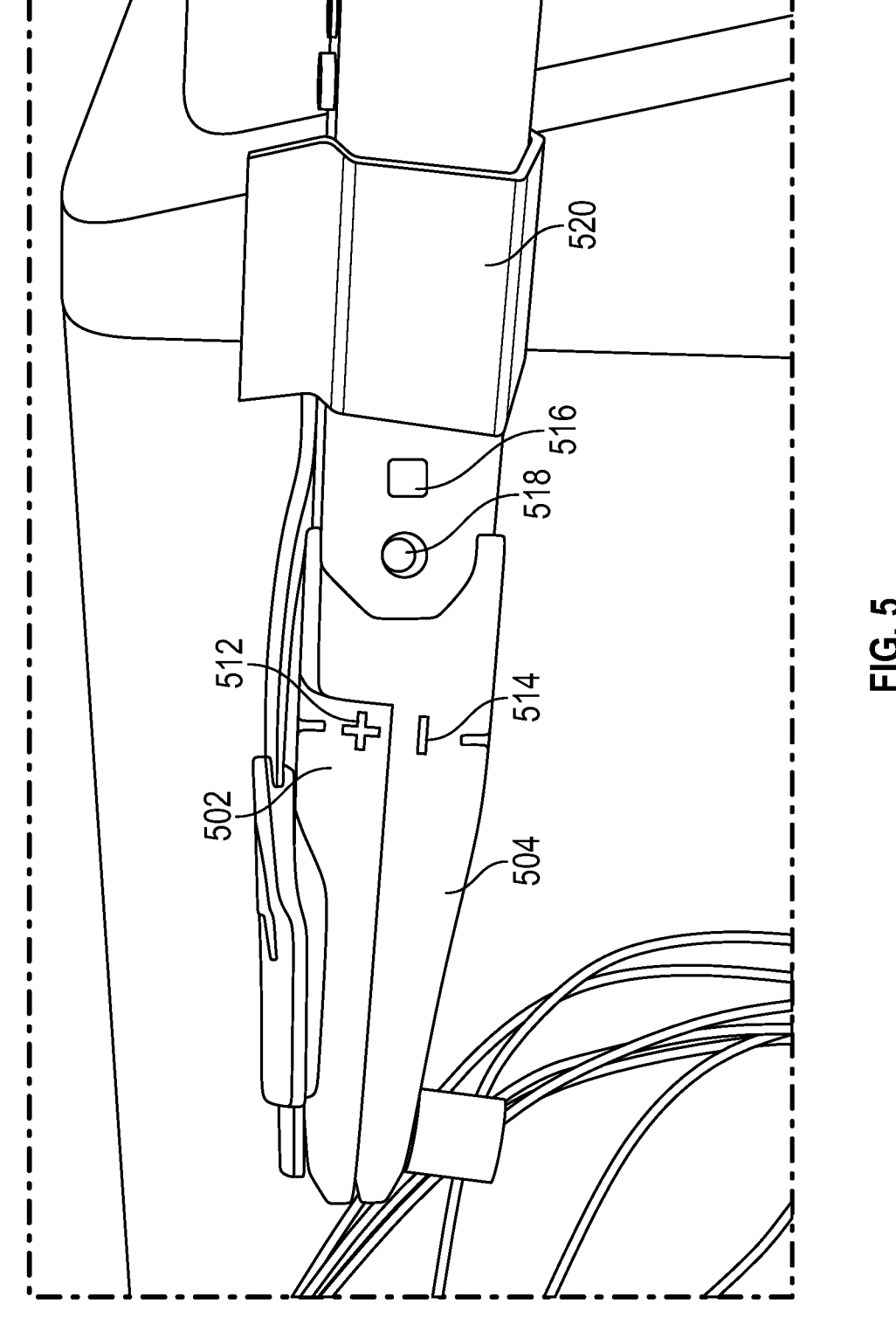
FIG. 5 is a pair of jaws of a surgical instrument of FIG. 1 in a closed configuration, according to an aspect of the present disclosure.
Figure 6:
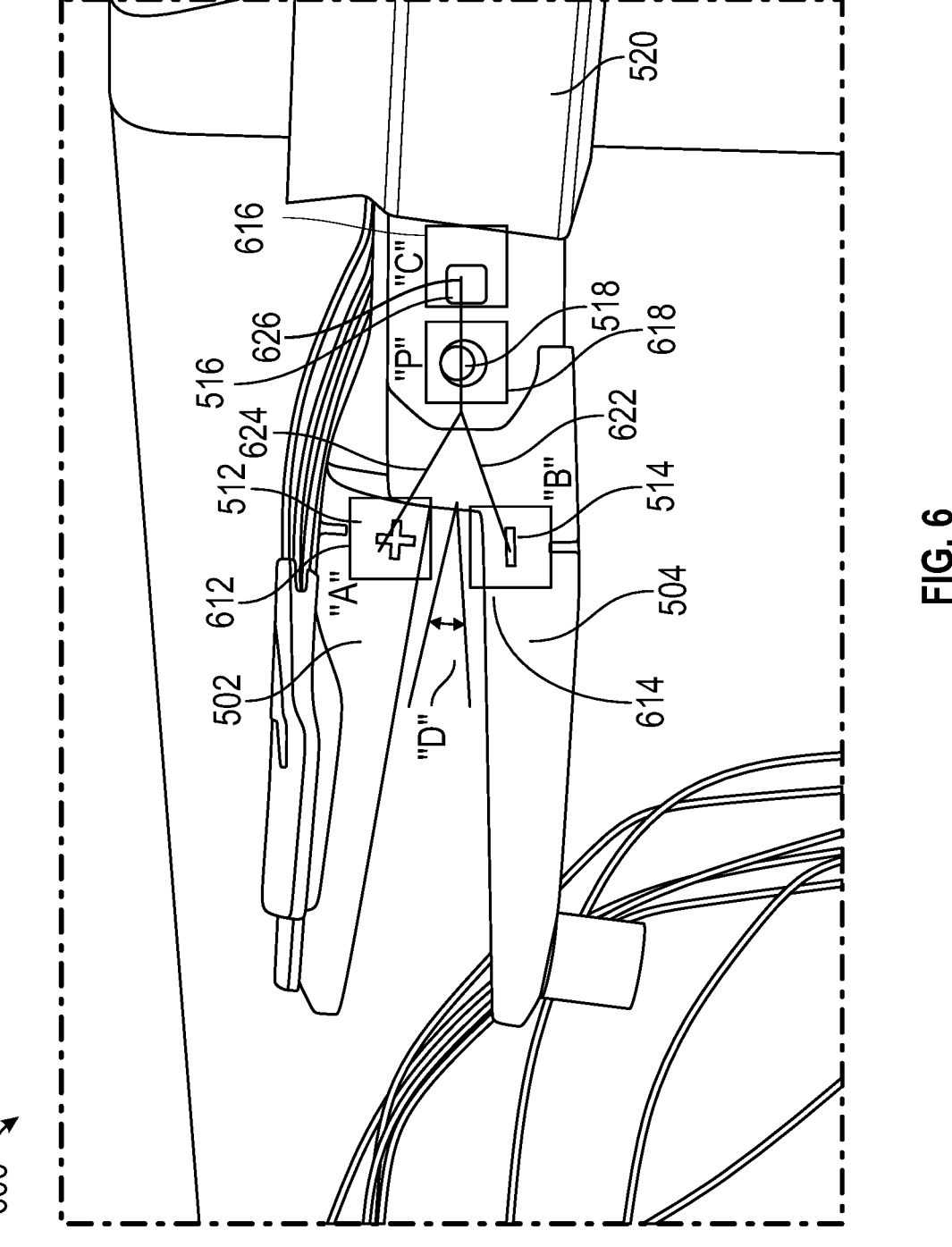
FIG. 6 is an image of identified markers of the jaws of FIG. 6 in an open configuration, according to an aspect of the present disclosure.

Referring to FIGS. 5 and 6, a pair of jaws 500 of an instrument (e.g., instruments 12 and 14) configured for operating at a surgical site is shown. The pair of jaws 500 are configured to grasp tissue and may include a moveable jaw 502, a fixed jaw 504, and a shaft 520. The lower jaw (i.e., fixed jaw 504) may be fixed, wherein its apex may be considered a fixed point in space, whereas the second jaw (i.e., moveable jaw 502) is configured to rotate so as to increase/decrease the opening of the jaws. In embodiments, both jaws 502 and 504 may be movable relative to each other.

The moveable jaw 502 and the fixed jaw 504 each include one or more distinct fiducial markers 512, 514, configured as a "target" during object detection (bounding boxes "A" 612, "B" 614). The shaft 520 may include one or more distinct fiducial markers 516, 518 configured as a "target" during object detection (bounding boxes "C" 616, "P" 618). The distinct fiducial markers 512, 514, 516, 518 may include, for example, shapes (e.g., circle, square, and/or triangle), symbols (e.g., "+" and/or "−"), letters, IR readable markers, barcodes, etc. In aspects of the present disclosure, each of the distinct fiducial markers 512, 514, 516, 518 is different from each other. For example, fiducial marker 512 may be a "+", fiducial marker 514 may be a "−", fiducial marker 516 may be a square shape, and fiducial marker 518 may be a circle shape.

The distinct fiducial markers 512, 514, 516, 518 may be used to determine a spatial position of each jaw of the pair of jaws 500. Determining a spatial position of each jaw of the pair of jaws 500 may allow determining a jaw opening angle "D" between the moveable jaw 502 and the fixed jaw 504. In aspects of the present disclosure, the jaw opening angle "D" may be used to determine the mass and/or size of the grasped tissue and/or to determine the distance between the tips of the two jaws 500.

In aspects of the present disclosure, a single straight marker may be used across the fixed jaw 504 and across the moving jaw 502.

Figure 7:
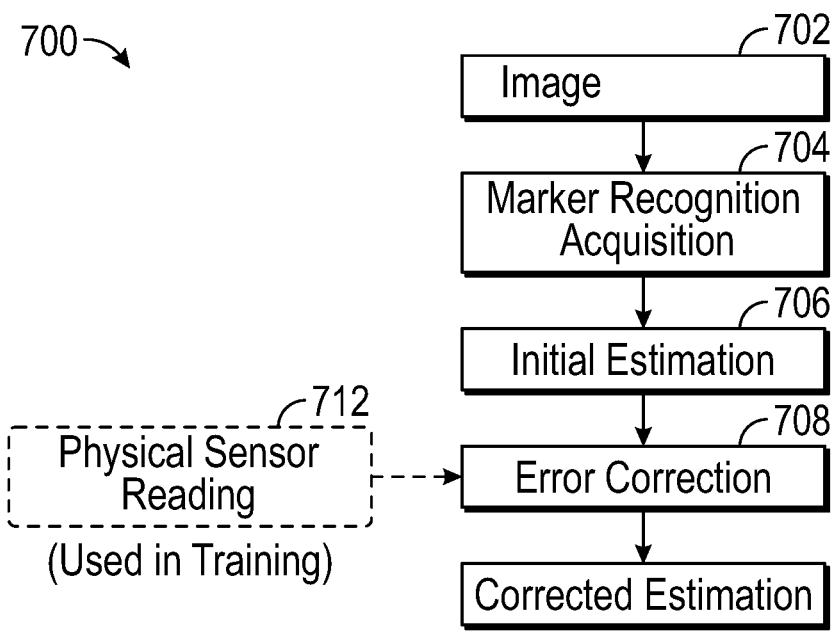
FIG. 7 is a flow chart of a method for controlling the energy-based surgical system of FIG. 1, according to an aspect of the present disclosure.
Figure 8:
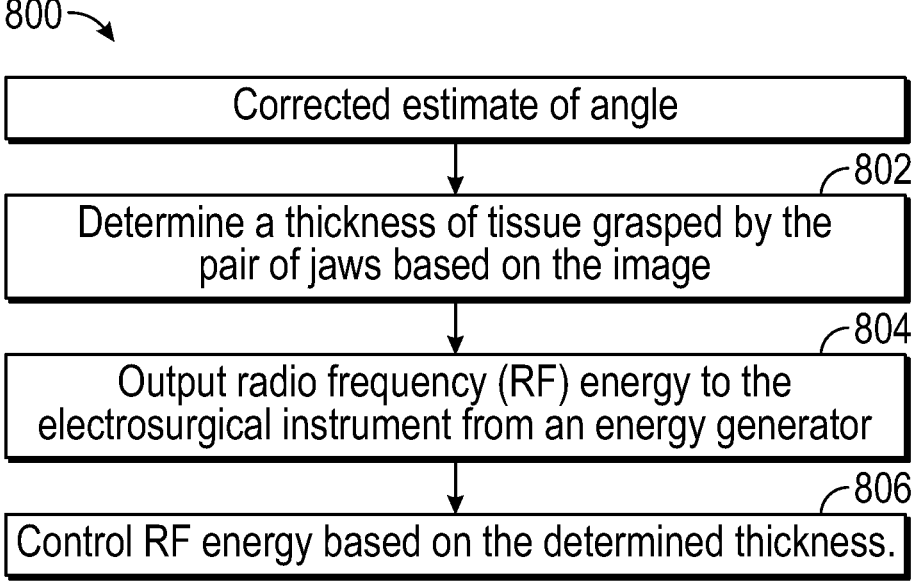
FIG. 8 is a flow chart of a method for controlling the energy-based surgical system of FIG. 1, according to an aspect of the present disclosure.

With reference to FIGS. 7 and 8, flow charts of operation of the endoscope controller 18 and the generator 100 includes detecting the instruments 12 and 14 to determine the mass and/or thickness of the tissue grasped by the instruments 12 and 14 and controlling the generator 100 based on the same. The flow charts of FIGS. 7 and 8 are described with respect to FIGS. 5 and 6, which show video frames captured by the endoscope 16.

At step 702, the endoscope 16 continuously captures and transmits video data of the surgical site which is displayed on the display 23 and/or display 32, depending on the system configuration being used.

At step 704, the endoscope controller 18 continuously processes the video data from the endoscope 16, and extracts visual cue data (e.g., identifying distinct fiducial markers). For example, the endoscope controller 18 may identify at least two of the distinct fiducial markers 512, 514, 516, 518 that are in the FOV of the endoscope 16, and generates bounding boxes "A" 612, "B" 614, "C" 616, and "P" 618 (FIG. 6) around the identified objects. In object detection, a bounding box is used to describe a target location (e.g., a fiducial marker). The fiducial marker identification may be performed by a neural network and/or other computer vision network. The markers may include IR readable markers and/or visible light readable markers.

Next, at step 706, the endoscope controller 18 performs an initial estimation of the jaw opening angle "D" (FIG. 6). The initial estimate may be performed by computing an angle between two adjacent line segments 622, 624 (FIG. 6) of interest. For example, the endoscope controller 18 may generate a first line segment that runs from bounding box "B" 614 through bounding box "P" 618 and a second line segment that runs from bounding box "A" 612 through bounding box "P" 618. This would result in a set of angle estimates that may include: ∠APB, ∠APC, BPC and a set of distance estimate |AP|, |BP|, and |CP|. For example, the endoscope controller 18 may estimate a jaw opening angle "D" of 25 degrees. In aspects of the present disclosure, the endoscope controller 18 also detects the state of the instruments 12 and 14, such as whether the jaws 500 are open or closed, and how open or closed they are based on the object identification.

Next, at step 708, the endoscope controller 18 performs error correction on the initial estimate of the jaw opening angle "D" using a correction network. The correction network is configured to predict correction values for the initial estimate of the jaw opening angle "D" and adjust the initial estimate based on the predicted correction values to provide a corrected estimate. The correction network may include a machine learning network. In aspects of the present disclosure, the correction network may be trained using physical sensor readings at step 712. Multiple physical sensor readings may be captured using a hardware sensor disposed on the tips of each of the pair of jaws 500 (FIG. 5) at arbitrary unknown and/or known camera angles. The correction network may correct for inaccuracies introduced by perspective distortion, marker location bias, and/or object detection errors. The distances between the distinct fiducial markers 512, 514, 516, 518 for a particular instrument 12, 14 may be a known fixed distance. When the endoscope controller 18 performs an initial estimation of the jaw opening angle "D" (FIG. 6), it may use the known fixed distances to aid in correcting for perspective error, thus enabling estimation of the angle with an image of the pair of jaws 500 that is at an arbitrary unknown camera angle. The correction network may try minimizing loss by analyzing the machine learning loss function, a geometrical loss function for device symmetry, a geometrical loss function for the three adjacent coplanar line segments 622, 624 and 626, and/or a geometrical loss function related to a constant distance between bounding boxes.

Figure 9:
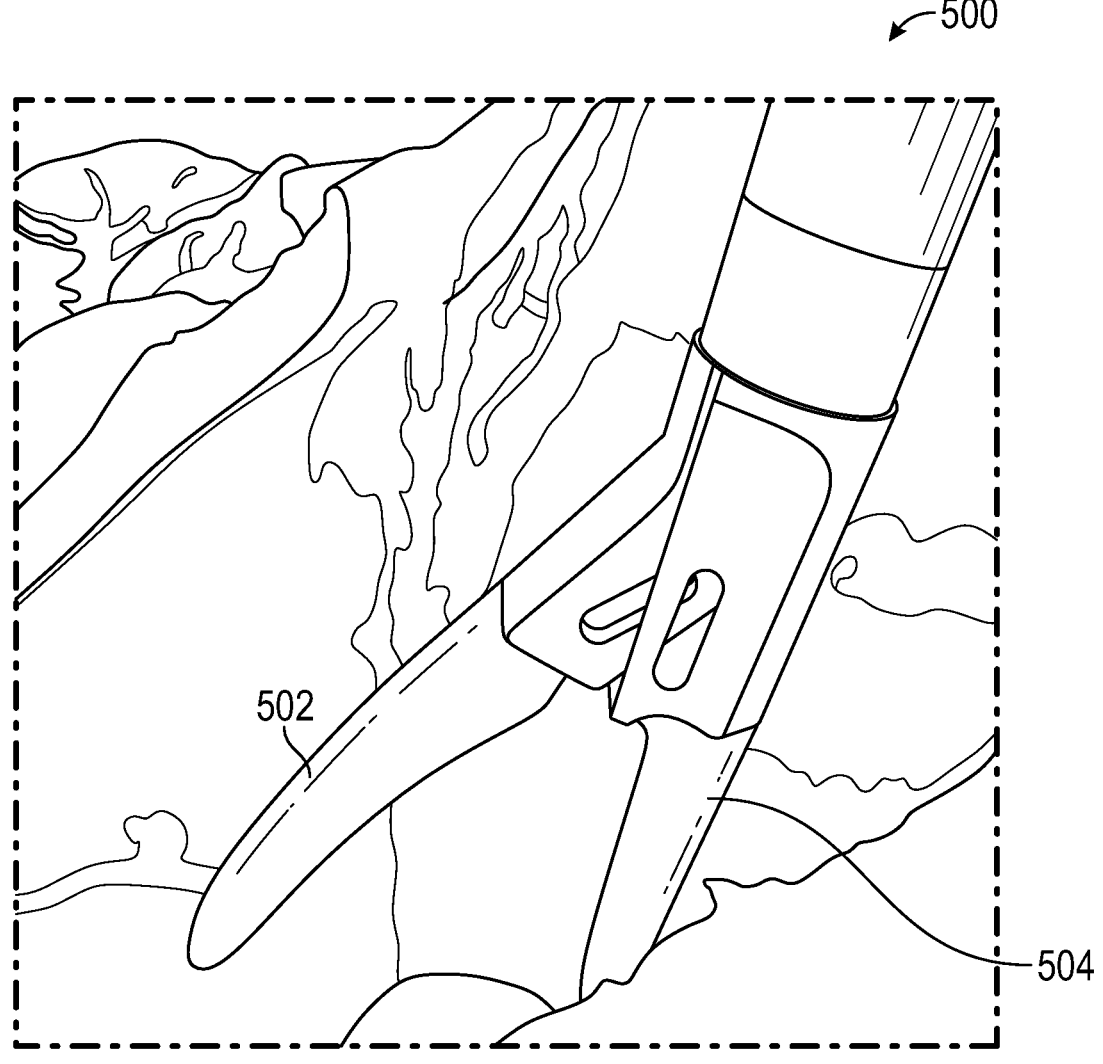
FIG. 9 is a depiction of the jaws of FIG. 6 grasping tissue.

Next, at step 802, the endoscope controller 18 determines a thickness of tissue grasped by the pair of jaws 500 (FIG. 9) based on the corrected estimate of the jaw opening angle "D." In aspects of the present disclosure, the endoscope controller 18 may determine tissue conductivity based on the tissue thickness. The endoscope controller 18 may also determine a tissue type based on estimated tissue conductivity derived from tissue impedance, tissue thickness, and an estimation of the jaw-tissue contact surface area. For example, uterine tissue has a different conductivity than liver tissue. The endoscope controller 18 may determine that the type of tissue grasped by the pair of jaws 500 is uterine tissue based on the determined impedance and the estimated angle when the contact surface area is controlled. The disclosed method may be advantageous when treating delicate tissue that is sensitive to thermal damage.

Next, at step 804, the endoscope controller 18 controls an energy generator 100 to output radio frequency (RF) energy to the electrosurgical instrument. In aspects of the present disclosure, the endoscope controller 18 may determine if the estimated angle is greater than a predetermined value and initiate an electrosurgical mode prior to initiating a seal cycle, based on the determination. The energy generator 100 may be configured to select the electrosurgical mode based on a configuration of the electrosurgical instrument 12, 14.

Next, at step 806, the endoscope controller 18 controlling RF energy based on the determined thickness and/or based on the determined tissue type. In aspects of the present disclosure, the endoscope controller 18 may adjust seal cycle parameters based on the estimated jaw angle. For example, the estimated angle, tissue thickness, and/or estimated tissue type may be used by the energy generator 100 to control energy delivery to the instrument 14 by changing the intensity of the energy. In aspects of the present disclosure, the endoscope controller 18 may be configured to adjust the intensity of the electrosurgical generator output by the generator 100. Adjustments may include changing the intensity of the preset intensity of the mode, stopping energy entirely, or directing energy in one direction away from the critical structure. In aspects of the present disclosure, the endoscope controller 18 may be configured to determine whether the tissue being operated on is within dimensional thresholds to avoid including too much tissue between pair of jaws 500 of instruments 12, 14.

In aspects of the present disclosure, the disclosed method may be used to augment intraoperative pathology consultation (e.g., assisting in cancer margin detection). Cancerous tissue is generally less conductive (higher resistance) than normal tissue largely due to the loss of water content inside of it. For example, a clinician may probe several locations to ensure she has an adequate margin prior to tissue resection.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. An energy-based surgical system comprising:
an electrosurgical instrument, including a pair of jaws;
an endoscope configured to capture image data of a surgical site including the electrosurgical instrument;
an energy generator coupled to the electrosurgical instrument, the energy generator configured to generate an energy output to the electrosurgical instrument; and
an endoscope controller including:
a processor; and
a memory including instructions stored thereon, which, when executed by the processor, cause the energy-based surgical system to:
access an image captured by the endoscope;
based on the captured image, determine an angle of the pair of jaws when grasping tissue;
determine a thickness and a tissue conductivity of the tissue grasped by the pair of jaws based on the angle of the pair of jaws; and
control the energy output of the energy generator based on the determined thickness.

2. The energy-based surgical system according to claim 1, wherein the electrosurgical instrument includes at least two markers, with one of the at least two markers being disposed on one of the jaws, wherein when determining the thickness of the tissue, the instructions, when executed, further cause the energy-based surgical system to:
recognize the at least two markers; and
estimate the angle of the jaws based on the recognized markers.

3. The energy-based surgical system according to claim 2, wherein the at least two markers include at least one of infrared readable markers or visible light readable markers.

4. The energy-based surgical system according to claim 2, wherein the instructions, when executed, further cause the energy-based surgical system to:
determine if the estimated angle is greater than a predetermined value; and
initiate an electrosurgical mode prior to initiating a seal cycle, based on the determination, wherein the energy generator is further configured to select the electrosurgical mode based on a configuration of the electrosurgical instrument.

5. The energy-based surgical system according to claim 4, wherein the instructions, when executed, further cause the energy-based surgical system to adjust seal cycle parameters based on the estimated jaw angle.

6. The energy-based surgical system according to claim 1, wherein when determining the thickness of the tissue, the instructions, when executed, further cause the energy-based surgical system to control the energy output of the energy generator based on the determined tissue conductivity.

7. The energy-based surgical system according to claim 1, wherein when determining the thickness of the tissue, the instructions, when executed, further cause the energy-based surgical system to determine tissue type based on the determined tissue conductivity.

8. The energy-based surgical system according to claim 7, wherein when determining the thickness of the tissue, the instructions, when executed, further cause the energy-based surgical system to control the energy output of the energy generator based on the determined tissue type.

9. The energy-based surgical system according to claim 1, wherein the determining of at least one of the tissue thickness or the tissue conductivity is performed by a machine learning network.

10. A computer-implemented method for controlling an energy generator, the method includes:

receiving image data of a surgical site and an electrosurgical instrument through an endoscope, the electrosurgical instrument including a pair of jaws;

estimating an angle of the jaws based on the received image;

determining a tissue type and a tissue thickness of tissue grasped by the pair of jaws based on the estimated angle;

outputting radio frequency (RF) energy to the electrosurgical instrument from an energy generator; and controlling RF energy based on the determined thickness.

11. The computer-implemented method according to claim 10, wherein the electrosurgical instrument includes at least two markers, with one of the at least two markers being disposed on one of the jaws, wherein when determining the thickness of the tissue the method further includes:

recognizing the at least two markers; and estimating the angle of the jaws based on the recognized markers.

12. The computer-implemented method according to claim 11, wherein the at least two markers include at least one of infrared readable markers or visible light readable markers.

13. The computer-implemented method according to claim 11, further comprising:

determining if the estimated angle is greater than a predetermined value; and initiating an electrosurgical mode prior to initiating a seal cycle, based on the determination, wherein the energy generator is further configured to select the electrosurgical mode based on a configuration of the electrosurgical instrument.

14. The computer-implemented method according to claim 13, further comprising adjusting seal cycle parameters based on the estimated jaw angle.

15. The computer-implemented method according to claim 10, wherein when determining the thickness of the tissue, the method further includes controlling the energy output of the energy generator based on the determined tissue type.

16. The computer-implemented method according to claim 10, wherein when determining the thickness of the tissue, the method further includes determining tissue type based on estimated tissue conductivity.

17. The computer-implemented method according to claim 16, wherein when determining the thickness of the tissue, the method further includes controlling the energy output of the energy generator based on the determined tissue type.

18. A computer-implemented method for controlling an energy generator, the method comprising:

receiving image data of a surgical site and an electrosurgical instrument through an endoscope, wherein the electrosurgical instrument includes a pair of jaws and at least two fiducial markers, with one of the at least two fiducial markers disposed on one jaw of the pair of jaws;

identifying the at least two fiducial markers within the image;

based on identifying the at least two fiducial markers, estimating an initial jaw angle of the pair of jaws while grasping the tissue;

performing an error correction on the initial estimate of the jaw angle using a machine learning network to generate a corrected estimate of the jaw angle;

based on the corrected estimate of the jaw angle, determining a thickness of tissue grasped by the pair of jaws and at least one of tissue type or tissue conductivity based on the image;

outputting radio frequency (RF) energy to the electrosurgical instrument from an energy generator; and controlling RF energy based on at least one of the determined thickness, tissue type, or tissue conductivity.

19. The computer-implemented method of claim 18, wherein the machine learning network is trained based on physical sensor readings captured from one or more hardware sensors disposed on at least one jaw of a surgical instrument.

* * * * *